United States Patent
Dai et al.

(10) Patent No.: US 8,062,901 B2
(45) Date of Patent: Nov. 22, 2011

(54) DEVICES AND METHODS FOR SAMPLE COLLECTION AND ANALYSIS

(75) Inventors: Jielin Dai, Hangzhou (CN); Haipeng Hu, Hangzhou (CN); Feier Liao, Hangzhou (CN); Weidong Yu, Hangzhou (CN); Shaomin Sun, Hangzhou (CN)

(73) Assignee: Alere Switzerland GmbH, Zug (CH)

( * ) Notice: Subject to any disclaimer, the term of this patent is extended or adjusted under 35 U.S.C. 154(b) by 1581 days.

(21) Appl. No.: 11/119,528

(22) Filed: Apr. 30, 2005

(65) Prior Publication Data

US 2006/0246598 A1    Nov. 2, 2006

(51) Int. Cl.
*G01N 33/48* (2006.01)

(52) U.S. Cl. ........ 436/165; 436/169; 422/401; 422/404; 422/409; 422/420

(58) Field of Classification Search .................. 422/401, 422/404, 409, 420, 63, 165, 169
See application file for complete search history.

(56) References Cited

U.S. PATENT DOCUMENTS

| | | |
|---|---|---|
| 3,996,006 A | 12/1976 | Pagano |
| 4,353,868 A | 10/1982 | Joslin |
| 4,473,079 A | 9/1984 | Jasper |
| 4,615,982 A | 10/1986 | Lawrence |
| 4,707,450 A | 11/1987 | Nason |
| 4,789,629 A | 12/1988 | Baker |
| 4,820,646 A | 4/1989 | Lawrence |
| 4,937,197 A | 6/1990 | Lawrence |
| 4,939,097 A | 7/1990 | Lawrence |
| 4,942,132 A | 7/1990 | Lawrence |
| 4,971,914 A | 11/1990 | Lawrence |
| 4,978,504 A | 12/1990 | Nason |
| 5,053,342 A | 10/1991 | Lawrence |
| 5,064,766 A | 11/1991 | Wardlaw |
| 5,068,197 A | 11/1991 | Lawrence |
| 5,070,014 A | 12/1991 | Dorn |
| 5,078,968 A | 1/1992 | Nason |
| 5,081,040 A | 1/1992 | Patel |
| 5,149,506 A | 9/1992 | Skiba |
| 5,171,528 A | 12/1992 | Wardlaw |

(Continued)

FOREIGN PATENT DOCUMENTS

EP    0727653 A2    8/1996

(Continued)

OTHER PUBLICATIONS

"Test Instructions: Miscellaneous Tests: Fecal Occult Blood Test Dipstrip" from www.meditests.com/t-misc2.html.

(Continued)

*Primary Examiner* — Lyle Alexander
(74) *Attorney, Agent, or Firm* — DLA Piper LLP (US)

(57) ABSTRACT

The present invention provides devices, methods, and kits for the collection of a solid or semi-solid sample and analysis for the presence, absence, or quantity of an analyte. The invention provides a collection slide having a first card and a second card. The first card has a sample collection area. The first and second cards have orifices allowing the passage of fluid through the sample collection area, and the cards are hingeably connected to each other. The invention also provides an assay device having a housing with a test element, a results window, and a docking area for receiving and engaging the collection slide. In one embodiment the collection slide and device can be used to detect the presence of fecal occult blood (human hemoglobin) in a stool sample. Many other embodiments are described herein.

7 Claims, 6 Drawing Sheets

U.S. PATENT DOCUMENTS

| | | |
|---|---|---|
| 5,192,501 A | 3/1993 | Guadangno |
| 5,196,167 A | 3/1993 | Guadangno |
| 5,217,874 A | 6/1993 | Guadangno |
| 5,246,669 A | 9/1993 | Hayashi |
| 5,264,181 A | 11/1993 | Schreiber |
| 5,306,270 A | 4/1994 | Macartney |
| 5,310,680 A | 5/1994 | Baker |
| 5,331,973 A | 7/1994 | Fiedler |
| 5,337,426 A | 8/1994 | Matusewicz |
| 5,391,498 A | 2/1995 | Baker |
| 5,412,819 A | 5/1995 | Matusewicz |
| 5,416,025 A | 5/1995 | Krepinsky |
| 5,447,868 A | 9/1995 | Augurt |
| 5,514,341 A | 5/1996 | Urata |
| 5,543,115 A | 8/1996 | Karakawa |
| 5,563,071 A | 10/1996 | Augurt |
| 5,702,913 A | 12/1997 | Guadagno |
| 5,747,351 A | 5/1998 | Hemmati |
| 5,846,838 A | 12/1998 | Chandler |
| 5,882,942 A | 3/1999 | Kagaya |
| 5,948,687 A | 9/1999 | Cleator |
| 5,975,373 A | 11/1999 | Forsberg |
| 6,057,166 A | 5/2000 | Childs |
| 6,168,758 B1 | 1/2001 | Forsberg |
| 6,207,113 B1 | 3/2001 | Kagaya |
| 6,221,678 B1 | 4/2001 | Chandler |
| 6,268,136 B1 | 7/2001 | Shuber |
| 6,271,046 B1 | 8/2001 | Chandler |
| 6,293,435 B1 | 9/2001 | Forsberg |
| 6,410,336 B1 | 6/2002 | Augurt |
| 6,436,714 B1 | 8/2002 | Clawson |
| 2001/0004532 A1 | 6/2001 | Chandler |
| 2004/0019295 A1 | 1/2004 | Zhou |
| 2004/0019298 A1 | 1/2004 | Zhou |
| 2004/0184996 A1 | 9/2004 | Rabinowitz |
| 2005/0036910 A1 | 2/2005 | Zhou |
| 2005/0158869 A1 | 7/2005 | Chandler |
| 2005/0158878 A9 | 7/2005 | Chandler |

FOREIGN PATENT DOCUMENTS

| | | |
|---|---|---|
| EP | 0727653 B1 | 8/1996 |
| EP | 1384442 A1 | 1/2004 |
| JP | 05093722 A2 | 4/1993 |
| JP | 07012808 A2 | 1/1995 |
| JP | 200258308 | 9/2000 |
| WO | WO 90/03927 | 4/1990 |
| WO | WO90/13802 A1 | 11/1990 |
| WO | WO92/11536 A1 | 7/1992 |
| WO | WO93/05387 A1 | 3/1993 |
| WO | WO94/22017 A1 | 9/1994 |
| WO | WO95/08120 A1 | 3/1995 |
| WO | WO 99/18436 | 4/1999 |
| WO | WO99/56103 A1 | 11/1999 |
| WO | WO00/10008 A1 | 2/2000 |
| WO | WO00/54029 A1 | 9/2000 |

OTHER PUBLICATIONS

Package Insert for "Hemo-Pack® Fecal Occult Blood Test," Syntron Bioresearch, Inc.

DEVICES AND METHODS FOR SAMPLE COLLECTION AND ANALYSIS

FIELD OF THE INVENTION

The present invention is directed to devices for the collection of solid or semi-solid biological samples, and their analysis for the presence of analytes.

BACKGROUND OF THE INVENTION

The following Background of the Invention is intended to aid the reader in understanding the invention and is not admitted to be prior art.

The detection of occult blood in stool samples is a preliminary method of detecting colon cancer. Traditional methods that detect hemoglobin in a stool sample, such as Guaiac-based chemical methods, are hampered by their inability to distinguish between dietary-derived hemoglobin (i.e. from meat in the diet) and human hemoglobin, which leads to a large number of false-positive test results. To over-come this difficulty, immunoassays specific for human hemoglobin (hHb) have been developed. The antibodies used in these assays are able to distinguish between hemoglobin derived from a human and that from another animal.

The collection and analysis of occult blood samples presents the problem of the unpleasantness of sample collection and analysis. Presently available devices fail to adequately solve these problems. Therefore, there is a clear and persistent need for a device that reduces the interaction of both the patient and the test operator with the sample while at the same time accurately detecting the presence of hHb in the sample.

SUMMARY OF THE INVENTION

The present invention provides devices, methods, and kits for collection and analysis of a biological sample. In one embodiment, the biological sample is a stool sample. One aspect of the invention is a collection slide having two cards that are hingeably connected. On the inner surface of a card is a sample collection area for deposition of the biological sample. The cards also contain orifices so that buffers can be passed through the cards and through the sample collection area, to elute analytes of interest from the sample contained in the cards. The present invention also provides a device for detecting an analyte in a biological sample. The device contains a test element, such as a test strip, having reagents for detecting the analyte. The device also contains a docking area for receiving the collection slide. In the docking area is a sample transfer orifice having an absorbent transfer material, which receives buffer passed through the orifices of the collection slide, and passes the eluted fluid to the test element.

In a first aspect the present invention provides a device for detecting an analyte in a sample. The device has a housing containing a test element, and a docking area on the housing for receiving and engaging a collection slide. The docking has a sample transfer orifice with an absorbent transfer bead disposed therein and in fluid communication with the test element. The device also has a results window for observing a test result.

The transfer material can be made of a variety of materials or shapes. In various embodiments the transfer material is ultra-high molecular weight polyethylene, polyethylene, polyurethane, nylon, polyester, polypropylene, polytetrafluoroethylene, or a cellulose-based material. In one embodiment, the transfer material is an ultra-high molecular weight polyethylene filter.

In one embodiment the sample transfer orifice of the device is a well situated in the housing of the device. The well is an indentation in the housing and serves to collect fluid that overflows from the absorbent transfer material. The absorbent transfer material can also contain reagents for improving the transfer of analyte from the collection slide to the test element. In one embodiment, the transfer material includes a reagent selected from the group consisting of: a surfactant, a protein, a buffer, a polymer and a preservative. A "surfactant" is a chemical compound that reduces the surface tension between two liquids. Surfactants can have a hydrophilic (attracted to water) group and a hydrophobic (repelled by water) group. "Proteins" are large molecules composed of one or more chains of amino acids in a specific order and folded shape determined by the sequence of nucleotides in the gene encoding the protein. A "buffer" is a solution containing either a weak acid and its salt or a weak base and its salt, and is resistant to changes in pH. A "polymer" can be any of numerous natural and synthetic compounds of usually high molecular weight consisting of up to millions of repeated linked units, each a relatively light and simple molecule. A "preservative" is an additive used to protect against decay, discoloration, or spoilage.

In another embodiment, the transfer material contains a reagent. In various embodiments the reagent can be any one or more of: a blocking agent, a surfactant, a wetting agent, a solubilizer, a stabilizer, a diluent and a preservative. "Blocking agents" can be any of a number of compounds or substances that bind to an analyte or a support media, and thereby prevent binding of an analyte to the support media. "Wetting agents" are usually organic based materials that modify the surface tension of liquids and help to provide a uniform coating on hard-to-wet or hydrophobic surfaces. "Stabilizers" are compounds that prevent degradation of the tertiary structure of compounds. For example, compounds can be added to the collection slide to prevent decomposition of the Hb molecules in the sample, or of specific binding molecules in the device.

In a further embodiment, the transfer bead comprises a reagent selected from the group consisting of BRIJ® 35, Chemal LA-9, Pluronic® L64, Surfactant 10G, Span® 60, Silwet® L7600, Rhodasurf ON-870, Cremohor® EL, Tween® 20, Tween® 80, Surhynol® 485, Igepal® CA210, Triton® X-45, Triton® X-100, Triton® X-305, Bio-Terge® AS-40, Standapol ES-1, Benzalkonium Chloride, Tetronic® 1307, Surynol® 465, Ninate® 411, Pluronic® F69, Zonyl® FSN 100, AEROSOL® OT 100%, Geropon® T77, sodium dodecylsulfate, sodium taurocholate, sodium cholate, CTAB, LDAO, CHAPS, NP40, n-octyl sucrose, n-dodecyl sucrose, n-dodecyl maltoside, octyl glucoside, octyl thioglucoside, n-hexyl glucoside, n-dodecyl glucoside, Tris(hydroxymethyl) aminomethane buffer, phosphate buffer, borate buffer, tartrate buffer, phthalate buffer, PVP K-30, PVP K-90, GANTREZ® AN-119, polyethylene oxide, polyelthylene glycol, PEG 800, GANTREZ® AN-119, polyvinylalcohol, PVP/VA S630, bony fish gelatin, crosslinked polyacrylic acid polymer, hydroxyporpylcellulose, sodium carboxymethylcellulose, sodium polystryenesulfonate, sodium carageenin, acrylic latex, hydroxyethylcellulose, bovine serum albumin, egg white albumin, casein, ProClin® 300 and sodium azide.

In another embodiment, the test element is present within the housing and is a bibulous matrix having a sample application zone in fluid communication with the absorbent transfer material. The test element has a reagent zone containing reagents for conducting an assay, and a detection zone having a test line for visually detecting the presence or absence of the analyte at the test line. The test line can have a specific binding molecule for the analyte immobilized on the matrix. In one embodiment, the analyte of interest is human hemoglobin and the specific binding molecule on the test line binds to human hemoglobin. The reagent zone can contain a labeled specific binding molecule for the analyte, which in one embodiment is an antibody. The specific binding molecule can be present in a dried form, and can be solubilized by the passing sample fluid. In another embodiment the test line has reagents for conducting a chemical test.

In certain embodiments, the docking area has one or more snap locks for holding a sample collection slide in position in the docking area. For example, the docking area can have projections for securing a sample collection slide in position above the absorbent transfer pad. By "snap lock" is meant one or more projections through which the collection slide fits tightly. Thus, when the collection slide is moved into place, it will "snap" into position past the "snap locks." The projections can project into the area of the docking area. The docking area can also be an area into which the collection slide is inserted in a sliding motion. In either embodiment, the eluent orifice of the collection slide is brought into liquid communication with the absorbent transfer material. The docking area can be present as a depression or depressed portion of the housing, which is at least partially circumscribed by a raised area of the housing. Alternatively, the docking area can be present as a raised portion of the housing.

In another aspect, the present invention provides a collection slide for collecting and transferring a sample. The collection slide has a first card having an inner surface and a eluent orifice, and a second card hingeably connected to the first card and having an inner surface and a solvent orifice. The collection slide has an open position and a closed position, where the solvent and eluent orifices are aligned when the collection slide is in the closed position. The collection slide also has a sample collection pad on the first card, to which sample is applied for collection. In one embodiment the sample collection pad is present between the solvent and eluent orifices when the collection slide is in the closed position. The first and second cards can be made of a water-resistant or water-impermeable material. In one embodiment, the first and second cards are made of plastic.

In one embodiment, the sample collection area further has a collection pad overlaying the eluent orifice on the first card, with the sample application area at least partially circumscribed by a sealing structure on the first card. The second card can have a cover pad overlaying the solvent orifice, where the second card also has a sealing structure, complementary to the structure on the first card. In one embodiment, the structure on the first card is a gasket, which engages the structure on the second card, which is a groove, when the collection slide is in the closed position. By the two structures "engaging" is meant that a barrier is formed by their interaction which impedes the movement of sample into or out of the sample collection area. "Sealing structures" are those which impede the movement of sample into or out of the sample collection area when engaged. In an alternative embodiment, the first card can have the groove and the second card can have the gasket. Also, some embodiments utilize other structures, for example ridges that are generally sealed when the first and second card are in the closed position, or other structures. In a further embodiment, the first card or second card contains one or more holes for receiving a projection from the second card or first card, respectively, to retain the slide in a closed position. The cover pad and sample collection pad can be made of any suitable material. In some embodiments the cover pad and sample collection pad are made of a fibrous or bibulous material.

In another embodiment of the collection slide, the cover pad and/or collection pad contain reagents for eluting analyte from the sample. In certain embodiments, the reagent can be one or more of surfactants, buffers, proteins, polymers and preservatives, or a blocking agent, a surfactant, a wetting agent, a solubilizer, a stabilizer, a diluent and a preservative. Examples of useful reagents include BRIJ® 35, Chemal LA-9, Pluronic® L64, Surfactant 10G, Span® 60, Silwet® L7600, Rhodasurf ON-870, Cremohor® EL, Tween® 20, Tween® 80, Surhynol® 485, Igepal® CA210, Triton® X-45, Triton® X-100, Triton® X-305, Bio-Terge® AS-40, Standapol ES-1, Benzalkonium Chloride, Tetronic® 1307, Surynol® 465, Ninate® 411, Pluronic® F69, Zonyl® FSN 100, AEROSOL® OT 100%, Geropon® T77, sodium dodecylsulfate, sodium taurocholate, sodium cholate, CTAB, LDAO, CHAPS, NP40, n-octyl sucrose, n-dodecyl sucrose, n-dodecyl maltoside, octyl glucoside, octyl thioglucoside, n-hexyl glucoside, n-dodecyl glucoside, Tris(hydroxymethyl) aminomethane buffer, phosphate buffer, borate buffer, tartrate buffer, phthalate buffer, PVP K-30, PVP K-90, GANTREZ® AN-119, polyethylene oxide, polyethylene glycol, PEG 800, GANTREZ® AN-119, polyvinylalcohol, PVP/VA S630, bony fish gelatin, crosslinked polyacrylic acid polymer, hydroxypropylcellulose, sodium carboxymethylcellulose, sodium polystryenesulfonate, sodium carageenin, acrylic latex, hydroxyethylcellulose, bovine serum albumin, egg white albumin, casein, ProClin® 300 and sodium azide.

In another aspect, the present invention provides methods of detecting the presence or absence of an analyte in a sample contained in a sample collection slide. The methods involve placing a collection slide containing the sample into a docking area of a device for detecting analyte in a sample. The device and collection slide used in the methods are any as described herein. Additional steps of the methods involve applying an extraction buffer to the solvent orifice of the collection slide, allowing the extraction buffer to pass through the sample area and into the absorbent transfer bead and test element, and observing a test result in the results window.

In another aspect, the present invention provides kits for collecting and analyzing a biological sample. In one embodiment, the kits contain at least one collection slide as described herein, and a device for detecting an analyte in a fluid as described herein, provided in a package. In additional embodiments, the kits can contain one or more sample collector(s) as described herein, an envelope for containing a loaded collection device, and instructions for use, provided in a package. In various embodiments the kits can contain the sample collection slide, the device, and one or more of any of the additional components described. Any of the kits can also contain one or more bottles containing buffers for conducing an assay according to the instructions for use. In one embodiment the instructions for use are instructions for detecting the presence of hemoglobin in a feces sample.

In another aspect, the present invention provides methods of collecting a sample. The methods involve contacting a sample applicator loaded with sample with the sample collection pad of a collection slide as described herein, and placing the collection slide in the closed position. In some embodiments the methods also involve placing the closed collection slide containing the collected sample into an envelope or desiccation chamber. The placing of the collection slide into the closed position can include the step of pressing the first card and second card together to engage the one or more projections into one or more holes and locking the collection slide in the closed position. The placing the collection slide into the closed position can cause excess sample to be excluded from the sample collection pad.

In one embodiment the sample collection applicator is a tool having a portion for collecting sample, and the portion for collecting sample has a plurality of holes for the drainage of a fluid portion of the sample. In one embodiment, the portion for collecting sample is primarily flat.

The present invention includes a variety of other useful aspects, which are detailed herein. These aspects of the invention can be achieved by using the articles of manufacture and compositions of matter described herein. With reference to the present disclosure, it will be further recognized that various aspects of the present invention can be combined to make desirable embodiments of the invention. In addition, a variety of other aspects and embodiments of the present invention are described herein.

The summary of the invention described above is not limiting and other features and advantages of the invention will be apparent from the following detailed description, as well as from the claims.

BRIEF DESCRIPTION OF THE DRAWINGS

FIG. 3A illustrates an opened collection slide, showing a cover pad 218 and a collection pad 216. FIG. 3B illustrates application of the sample 310 to the collection pad. FIG. 3C illustrates a closed collection slide.

DETAILED DESCRIPTION

In the following detailed description, reference is made to the accompanying drawings that form a part hereof, and in which is shown by way of illustration specific embodiments in which the invention may be practiced. It is understood that other embodiments may be utilized and structural changes may be made without departing from the scope of the present invention.

Collection Slide

The present invention provides collection slides for collecting a solid or semi-solid sample. In some embodiments the sample is a biological sample, such as a stool sample. The present invention also provides devices for detecting the presence of analytes in the sample, and methods for collecting the sample.

Figure 1:
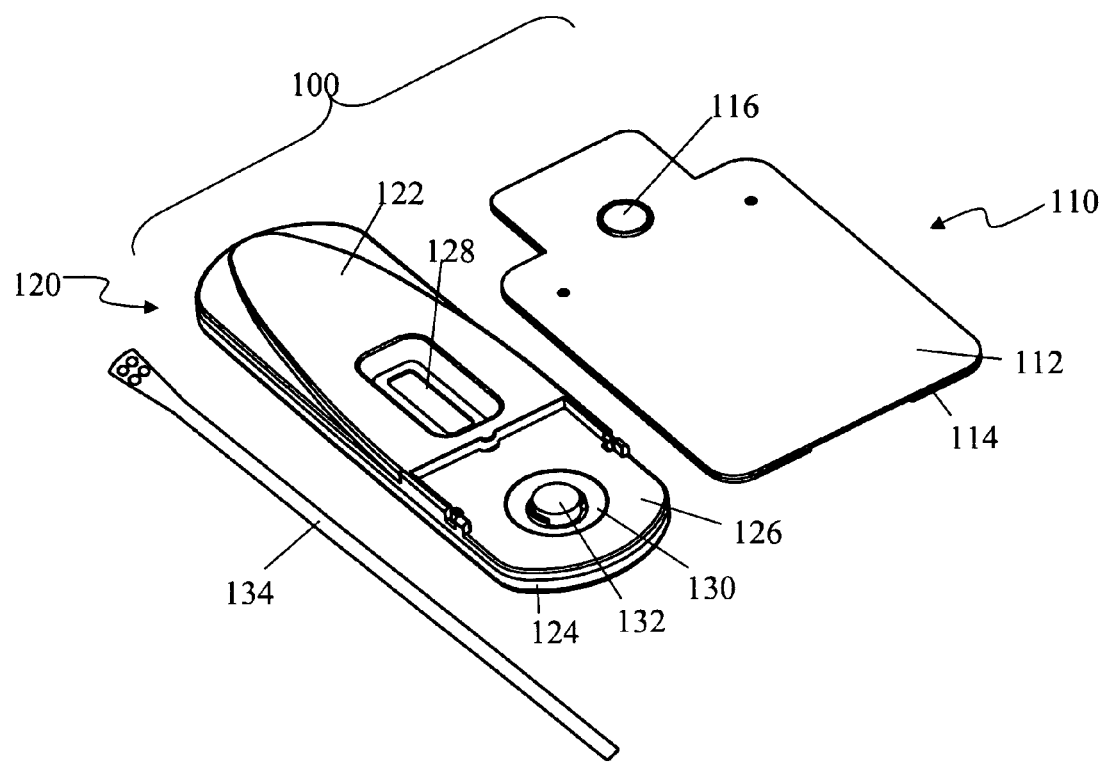
FIG. 1 provides a perspective view of the different aspects of the present invention 100, which includes a sample collection slide 110 and a test device 120 that engages the collection slide. Also shown is the sample collector 134 for applying the sample to the collection slide.
Figure 2:
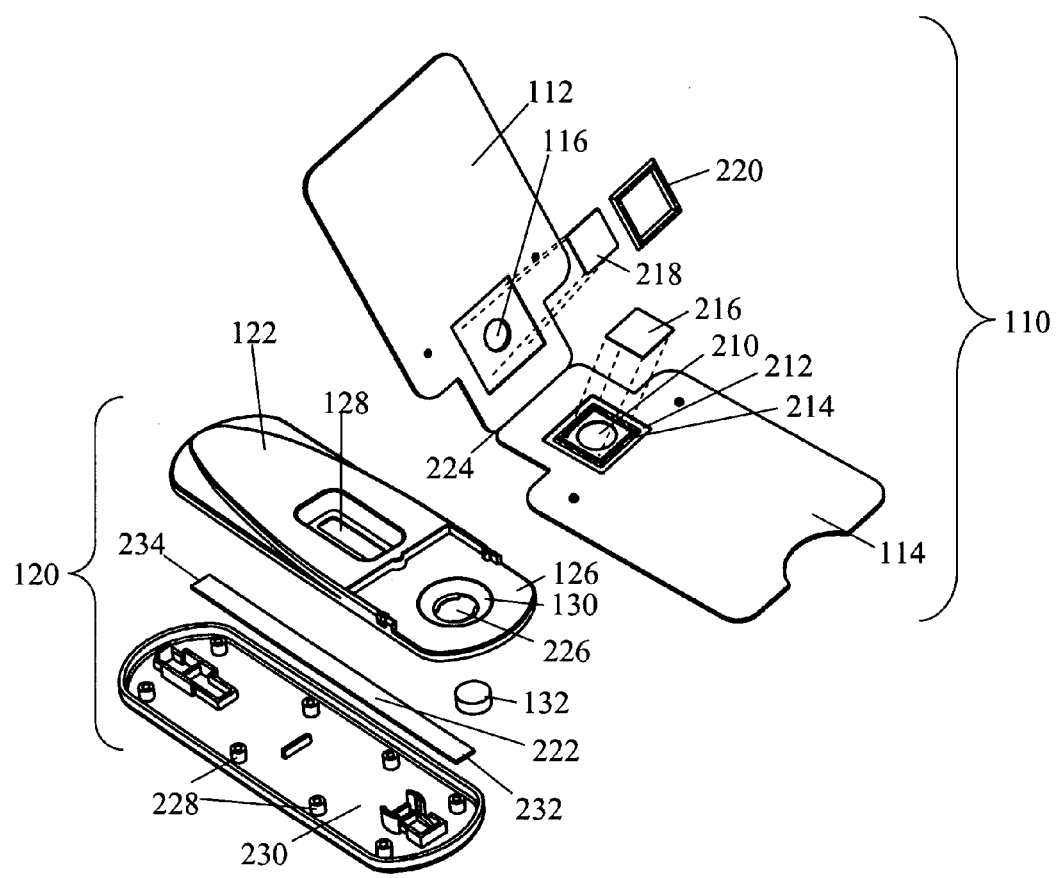
FIG. 2 provides and exploded view of the devices shown in FIG. 1.
Figure 3A:
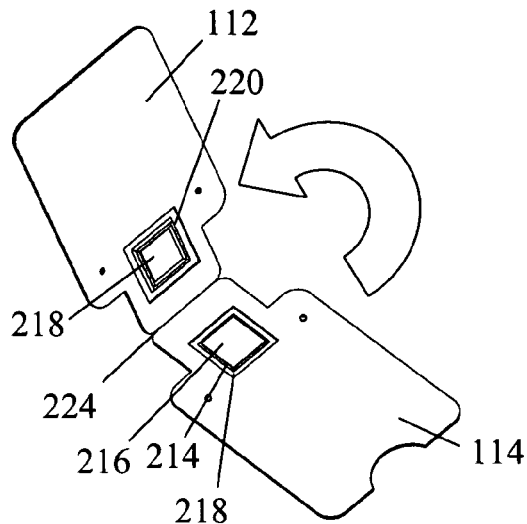
FIGS. 3A-3C illustrate application of a sample to the collection slide.
Figure 3B:
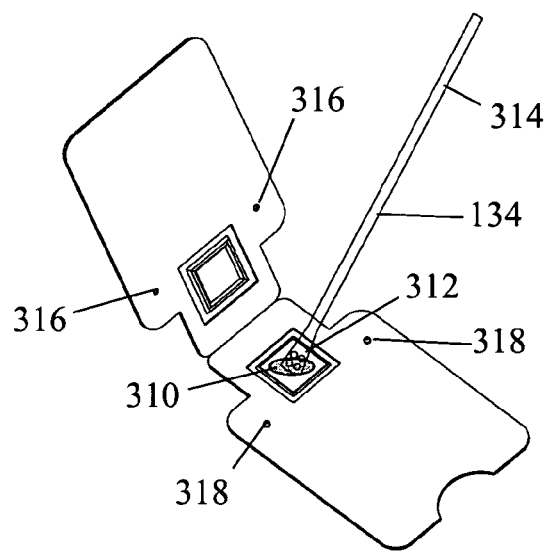
Figure 3C:
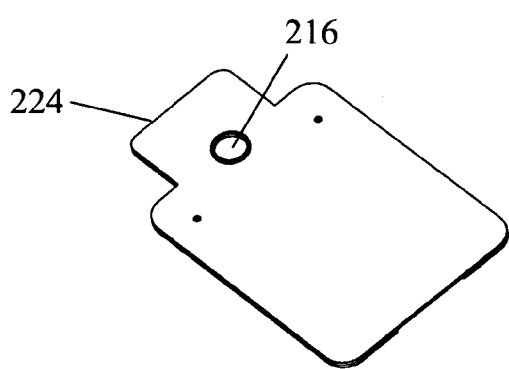
Figure 4:
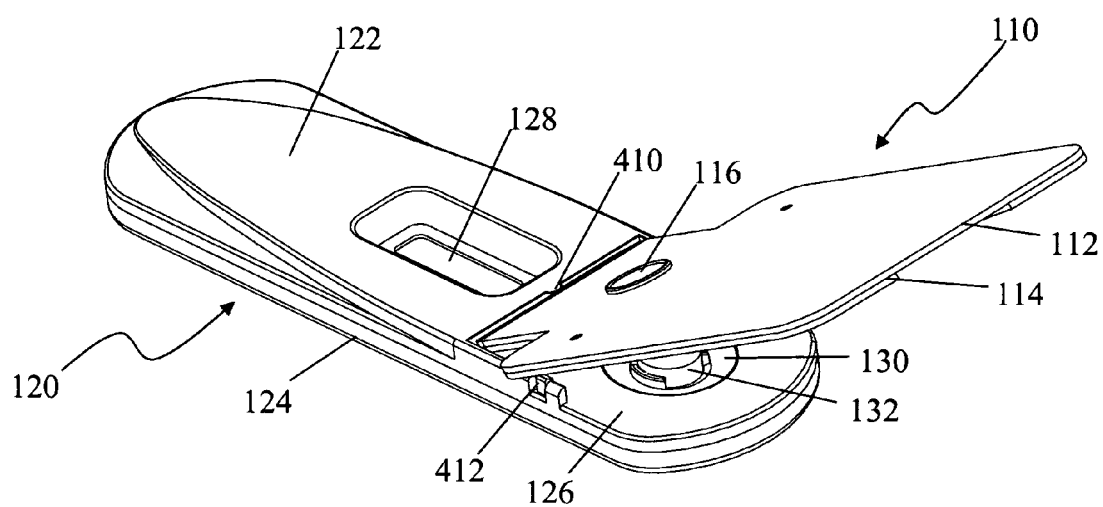
FIG. 4 illustrates a collection slide 110 engaging the docking area 126 of a test device.
Figure 5:
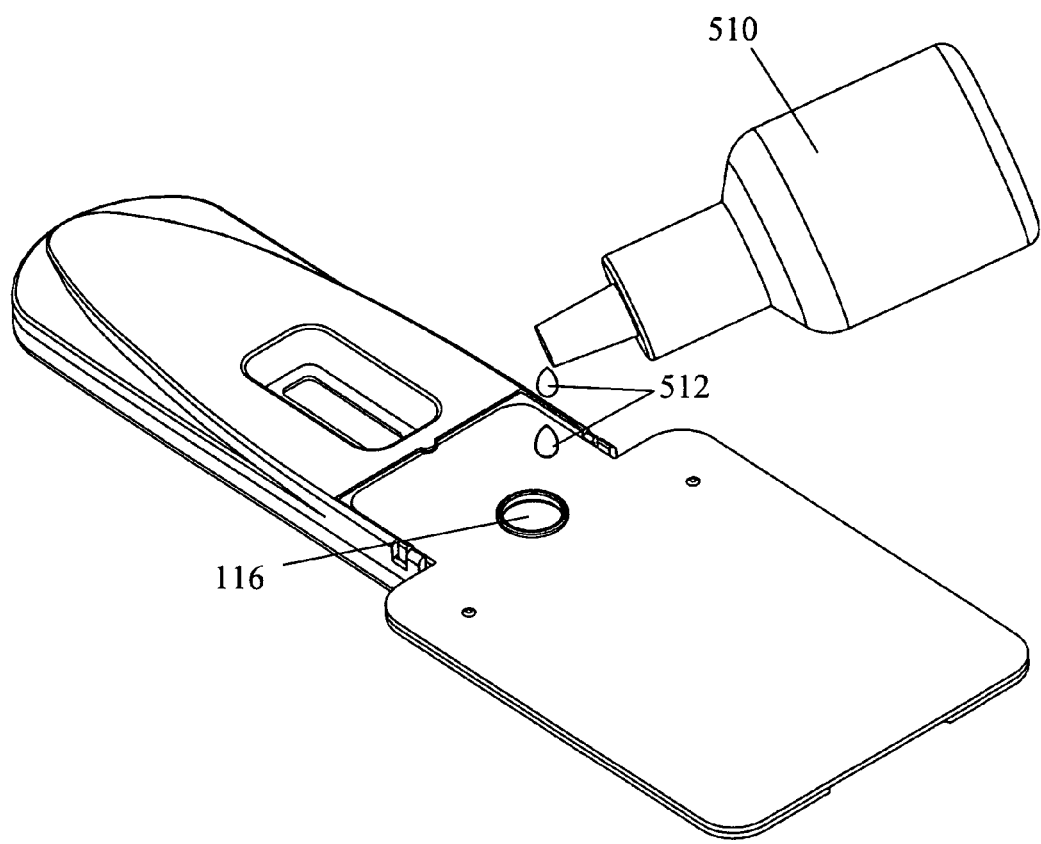
FIG. 5 illustrates application of extraction buffer 512 to the solvent orifice 116 of the engaged collection slide.

With reference to FIGS. 1-5, the collection slide 110 has a first card 114 and a second card 112. The first and second cards may be made of any appropriate material. For example, the cards can be made of a resilient, water resistant or water-impermeable material, such as plastic, coated cardboard, metal or glass. In one embodiment, the cards are hingeably connected to each other, for example by a hinge 224 (FIG. 2). By "hingeably connected" is meant that the two cards are connected to each other at their first ends and have free ends movable towards and away from each other by movement about the hinge. A wide variety of hinge connections may be advantageously used. In the exemplary embodiment shown in the figures, the collection slide is manufactured of injection molded plastic and the two cards are connected by a living hinge, as depicted in FIG. 2. In other embodiments, the hinge can be one or more flaps of material that bind the two cards together and allow for one card to be folded onto the other card. In another embodiment the cards are present as separate cards that can be secured together, for example by a locking mechanism. The second card has a buffer or solvent orifice 116, through which an extraction buffer 510, 512 can be applied to a collected sample (FIGS. 1 and 5).

The collection slide has an open position and a closed position (compare FIGS. 1 and 2). As illustrated in FIG. 2, the first card has an eluent orifice 210 and the second card has a solvent orifice 116. The buffer and eluent orifices are positioned on the cards so that when the collection slide is in the closed position, the two orifices are in alignment. By the orifices being "aligned" or "in alignment" is meant that a liquid applied to the solvent orifice in the second (or top) card in sufficient quantity will pass through the sample collection area and through the eluent orifice.

Referring to FIG. 2, a cover pad 218 is present on the inner surface of the second card and overlaying the buffer orifice 116. The cover pad and sample collection pad can be made of any suitable material that retains sample and allows the passage of fluid. Examples of materials suitable for the cover pad and/or sample collection pad are polyester mesh, fibrous or bibulous materials, paper or paper-based materials, synthetic fabrics, meshes and wools, coated or supported papers, polyesters, nylon membranes, nitrocelluose, glass wool, treated paper, absorbent paper, or a material made of a cellulose base. In the embodiment shown, the cover pad 218 is circumscribed by a gasket 220. With reference to the present disclosure the person of ordinary skill in the art will realize many other materials suitable for the cover pad and/or sample application pad.

On the first card is present an eluent orifice 210, which is overlaid with a sample collection pad 216. The sample collection pad 216 can be made of any suitable material that retains sample and allows for the passage of fluid. In various embodiments the sample collection pad 216 is made of the same types of materials as the cover pad. The sample collection pad can be circumscribed by ridge 214 and groove 212, or by a series of ridges and grooves. The cover pad and the collection pad can be made of any suitable material that retains sample and allows for the passage of fluid. Examples are provided above with respect to material for the cover pad. The material should also have sufficient resiliency to withstand the mechanical pressure of the sample application. Preferably, the material does not deteriorate or tear when wet.

Common difficulties with stool sample collection include that patients tend to over-apply sample to collection slides, which can cause interference when the assay is an immunoassay. The collection slide of the present invention limits the amount of sample that can be applied to the slide while requiring no direct sample manipulation by the technician conducting the test. The amount of sample collected is limited to the sample collection area, since the cover pad and sample collection pad are circumscribed by the sealing structures (e.g., a gasket and groove) when the slide is in the closed position. When the collection slide is moved to the closed position, the interaction of the sealing structures (e.g., the interaction of the gasket with the groove and ridge) separates the sample within the sample application area from sample applied outside the sample area. After the sample has been applied to the sample collection area, the collection slide is closed and retained in a locked position, thereby limiting the volume of sample retained within the sample area, because excess sample is squeezed out as the two cards are pressed together. The sealing structures can also be structures other than a gasket, ridge, and groove. For example, the structures can be a pressure sensitive adhesive or a wax bead (or beads) present on or around the sample collection pad and/or cover pad, which seal the sample collection pad when the two cards are closed and pressed together. The "seal" does not have to be a tight seal, just that it generally impedes the passage of sample into or out of the sample collection area when the collection slide is in the closed position. With reference to this disclosure the person of ordinary skill will realize many other structures that will find use in other embodiments of the invention.

The cover pad and/or collection pad can be treated with reagents that improve the flow of aqueous liquids through them. Additionally, these treatments also improve the elution of the analyte of interest from the dried sample within the sample area. In one embodiment the pads are treated with surfactants to inhibit proteins from sticking to the pads and to promote protein solubilization. A wide variety of commonly used anionic and non-ionic surfactants may be advantageously used in various concentrations. Some cationic and amphoteric surfactants may also find use in the present invention. Some examples of surfactants that may be used to treat the pads include, but are not limited to, the polyoxyethylene fatty ethers derived from lauryl, cetyl, stearyl and oleyl alcohols (e.g., the BRIJ® (ICI US, Inc.) series of surfactants). Other useful surfactants include octyl phenol ethoxylate surfactants (e.g., polyethyrene glycol mono-p-iso-octylphenyl ether and other Triton® (Rohm & Haas, Philadelphia, Pa.) series surfactants), polyoxyethylene derivatives of sorbitan esters (e.g., the Tween® (ICI Americas, Inc.) series of surfactants) and block copolymers based on ethylene oxide and propylene oxide and represented by $HO(C_2H_4O)_a(C_3H_6O)_b(C_2H_4O)_aH$ (e.g., the Pluronic® (BASF) series of surfactants). With reference to the present disclosure, a surfactant can be conveniently chosen using known surfactant selection techniques, such as by using a commercially available surfactant tool kit, for example, the Reagent Developer's Surfactant Took Kit (Pragmatics, Inc., Elkhart, Ind.), or a similar kit. These kits provide a convenient method of testing a large number of surfactants on a specific application, in order to optimize protein extraction and flow-through.

In some embodiments the pads may be treated with a buffer containing a component that improves analyte stability. Buffers can also condition the sample to promote optimal binding between the analyte and the specific binding reagents (e.g., antibodies or antibody fragments), which can be utilized in the assay. This can be performed, for example, by adjusting the pH of the analyte. Buffers having these useful qualities include, but are not limited to, Tris(hydroxymethyl) aminomethane buffer, phosphate buffer, borate buffer, tartrate buffer and phthalate buffer.

A "specific binding molecule" refers to a molecule that binds to a target analyte (e.g., human hemoglobin) and does not substantially bind to any other molecule present in the sample. In some embodiments a specific binding molecule can also bind to a molecule that correlates with or indicates the presence of an analyte of interest in a sample. By substantial binding is meant that binding occurs to an extent that will affect the result of an assay performed with the specific binding molecules, i.e., a less optimal or less accurate result will be obtained. A small amount of non-specific binding that may occur and that does not change the result of the assay is not considered substantial binding. In some embodiments the specific binding molecule can be an antibody or an antibody fragment (e.g., the Fab region of an antibody), an antigen, a receptor or fragment of a receptor that binds a ligand, or a member of a biotin-streptavidin pair or other type of binding pair.

The cover pad and/or sample application pad can also be treated with one or more polymers, which can also have the property of improving analyte stability and elution. Polymers sometimes used in protein purification can be useful for this purpose. Examples of useful polymers include, but are not limited to, polyvinylpyrrolidone (PVP), poly(methylvinylether-co-maleic anhydride, polyethylene oxide (PEO), polyelthylene glycol (PEG), copolymers of methyl vinyl ether and maleic anhydride (e.g., poly(methylvinylether-co-maleic anhydride), polyvinylalcohol (PVA), vinylpyrrolidone/vinylacetate, bony fish gelatin (from fish of the class Osteichthyes), crosslinked polyacrylic acid polymer, hydroxypropylcellulose (HPC), sodium carboxymethylcelluose (CMC), sodium polystyrenesulfonate, sodium carageenin, acrylic latex, and hydroxyethylcellulose (HEC)). These polymers are commercially available (e.g., from Pragmatics, Inc., Elkhart, Ind.), and are conveniently formulated in a polymer tool kit. They can therefore be used systematically to determine the advantages of particular polymers in particular applications.

To improve analyte extraction, the pads may also be treated with a non-specific protein, which functions as a blocking agent. Any protein may be used for this purpose including, but are not limited to, bovine serum albumin, egg white albumin, and casein.

The cover pad and sample application pad can also be treated with a preservative to increase the shelf-life of the collection slide. A "preservative" is a naturally or synthetically produced chemical added to inhibit microbial growth or undesirable chemical changes. Any preservative can be used that provides the preserving effect and does not interfere with the assay. Examples of useful preservatives include, but are not limited to, 5-chloro-2-methyl-isothiazol-3-one (e.g. ProClin® 300 (Supelco, Inc., Bellefonte, Pa.) and sodium azide. With reference to the present disclosure the person of ordinary skill will realize many other preservatives that will find use in the present invention.

The cover pad and collection pad form the top and bottom walls of the sample collection area, and serve to eliminate excess sample from the sample collection area. When the structures on the cards are a gasket, ridge, or groove, they can also be situated on the opposite cards as those described above.

In certain embodiments, one of the cards of the collection slide is provided with structures for securing the first and second cards in a closed position. In one embodiment short pins 316 (FIG. 3B) are present on the interior surface of one card. The opposite card is provided with holes 318 that mate with the pins. When the collection slide is closed, the pins are inserted into the holes and lodged with sufficient resistance to hold the collection slide in a closed or "locked" position. In one embodiment this action may advantageously cause a snapping noise, alerting the patient that the collection slide has been properly closed. Other methods of securing the collection slide in a closed position can also be incorporated into the slide. For example, a clip that fits over the outside of the two cards and holds them together could be used in one embodiment, or snaps present on the inner surfaces of the two cards can be used in another embodiment. With reference to the present disclosure the person of ordinary skill will realize other structures for retaining the collection slide in the closed position.

Sample Collector

The present invention also provides a sample collector 134 (FIG. 1). The sample collector has a handle 314 (FIG. 3) and a spatula 312 for moving the sample. In one embodiment the spatula is perforated with a plurality of holes, which reduces the liquid content of the sample, and also serves to reduce application of excess sample to the sample collection pad. In various embodiments the spatula portion of the device is perforated with 4, 5, 6, 7, 8, 9, 10, 11, 12, or more holes. The spatula portion of the collector can be generally flat, or can have a curved (spoon-like) shape. This device can be made of any suitable material (e.g., plastic). In one embodiment, the spatula portion of the device is made of a soft plastic, and the handle is made of a harder plastic. This will enable the spatula to bend when sample is applied to the sample collection pad and lay on the pad. The perforations in the spatula portion will also act as an aid in applying an even sample to the pad.

Methods of Collection

Another aspect of the present invention is methods of collecting a sample. In one embodiment the sample is a stool sample. The method of sample collection and operation of the collection slide and assay device is illustrated in FIGS. 3A-3C.

One embodiment of the methods is illustrated in FIG. 3A. The patient opens the collection slide to expose the inner surfaces of the first and second slides, revealing the cover pad and sample collection pad. A small amount of stool sample is applied to the sample collection pad 216. The collection slide is then closed (FIG. 3C). The present collection slide eliminates excess sample by providing a sample collection area, with a design such that only sample in the sample collection area will be incorporated into the assay. When the collection slide is closed, a structure the first card engages a structure second card, forming a wall that circumscribes the sample collection area. In one embodiment the structure on one card is a gasket, and the structure on the opposite card is a groove and a ridge. When the collection slide is in the closed position, the solvent or buffer orifice, the sample area, and the eluent orifice are all vertically aligned. In this position, when buffer is applied to the buffer orifice, it flows through the cover pad and into the sample collection area, and then out of the eluent orifice, thereby rinsing the sample in the process and solubilizing analyte of interest contained in the sample. Additionally, the buffer dilutes the sample and conditions it for optimal binding of analyte by the specific binding reagents on the test element. After passing through the eluent orifice, the liquefied sample is then passed into the absorbent transfer bead of the assay device.

It is known that human hemoglobin breaks down rapidly when left in a wet sample. To prevent analyte degradation, the methods can incorporate the step of drying the sample. This step can involve leaving the collection card exposed to air for a certain period of time to allow it to air dry, or drying the sample in an oven at 45° C. The step can also involve placing the closed collection slide into a container containing desiccant. The container can be a sealable pouch (e.g., a mailing pouch). After drying (or placing the collection slide in a sealable pouch containing a desiccant), the collection slide can be presented to a health care facility for analysis.

Assay Device

Another aspect of the present invention is an assay device 120 for analyzing a sample in the collection slide for the presence or absence of an analyte of interest (see FIGS. 1 and 2). One embodiment of the assay device is shown in FIGS. 1 and 2. In this embodiment the assay device has a housing consisting of a top portion 122 and a bottom portion 124, which engage one another and lock together. The housing may be constructed of any suitable material such as, for example, plastics, pressed hardboard, metals, ceramics, polymers (e.g., polycarbonate, polypropylene, cycloolefins), and other materials. In the embodiment illustrated in the Figures, the housing is made of molded plastic. The top and bottom portions can engage one another by any convenient means, such as parts that snap together, glue, micro-welding, and other means. In the embodiment illustrated in FIG. 2, the top portion has a series of pins on the inner surface (not shown) which snap-fit snuggly into a corresponding series of raised rings 228 on the inner surface 230 of the bottom portion, thereby securing the top and bottom portions of the assay device in a locked position.

A docking area 126 for receiving and engaging a collection slide is located on the assay device. The collection slide may be "loaded" meaning that it contains a sample to be analyzed. The docking area may be of any shape, and can mate with a portion of the collection slide carrying the sample collection area. In one embodiment the docking area can receive and engage an external collection slide. An external collection slide is one that can be loaded separated from the assay device, and is not physically connected to the device at the time of sample loading. By "receiving and engaging" a collection slide is meant that the assay device and collection slide are placed into the "test position." The "test position" is when the sample application pad and absorbent transfer material are in liquid communication.

The docking area can also receive the collection slide in reversible fashion, meaning that the collection slide can be removed from the device after buffers are applied and sample eluted from the collection slide. As illustrated in FIG. 4, in this embodiment the collection slide is snapped into the docking area by fitting the hinged edge of the collection slide under a tang 410. The collection slide is then pressed down onto the docking area and snapped into a locked position under one or more projections 412. The projections hold the collection slide flush with the docking area. In other embodiments the docking area is slided into the assay device. In one embodiment the docking area can have a part that fits over the collection slide to hold it in place. When in place, the sample collection pad and the absorbent transfer material are in fluid communication. The buffer orifice is exposed to receive buffer, and buffer applied to the buffer orifice passes through the sample collection pad and into the absorbent transfer material. In one embodiment the docking area is configures to receive the collection slide against an exterior surface of the assay device, so that the sample collection area and absorbent transfer member are brought into liquid communication. The docking area can have projections for holding the collection slide securing in the test position.

In other embodiments the docking area can receive the collection slide into the interior of the device. In another embodiment the sample transfer orifice is the only orifice in the assay device for receiving sample or assay fluids, and the sample and assay fluids both the device through the sample transfer orifice. "Assay fluids" refers to buffers or other regents utilized during the assay. Thus, in these embodiments the sample transfer orifice is the sole orifice for receiving sample and fluids into the device.

Figure 6:
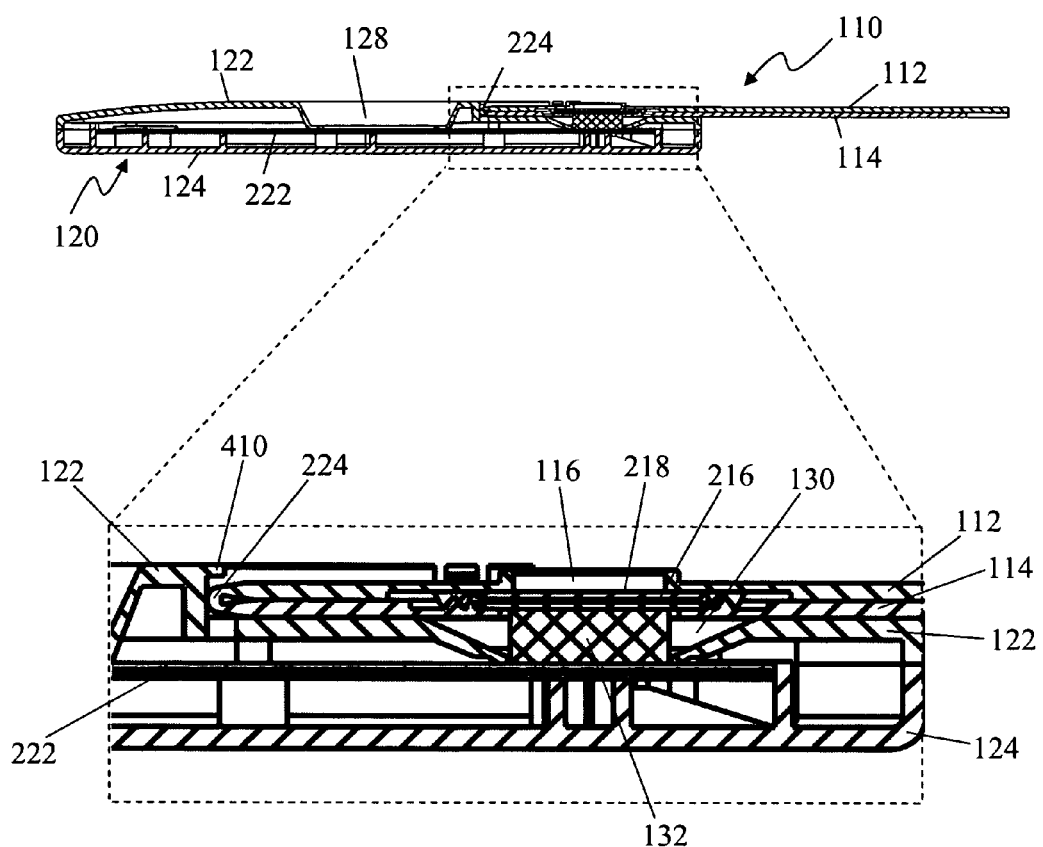
FIG. 6 provides a cross-sectional view of the collection slide 110 engaged in a test device 120.

As illustrated in FIG. 1, in one embodiment the docking area contains an indentation or well 130 having a transfer material 132 disposed therein. The absorbent transfer material can take any form, for example, a bead, cube, cylinder, oval, or any shape, and can be situated inside the well. As shown in FIG. 2, the transfer material protrudes through the top portion of the housing, through an orifice 226 to lie generally flush with or slightly protruding through the plane of the docking area. In this embodiment the absorbent transfer material is an absorbent transfer bead. Referring to FIG. 6, when the collection slide is snapped into the docking area, the buffer orifice, cover pad, sample collection pad, eluent orifice, and absorbent transfer bead are all generally in vertical alignment with each other. In this embodiment the absorbent transfer bead projects into or through the plane of the docking area, so that the absorbent transfer bead and the outer surface of the sample collection pad are placed into fluid communication through the eluent orifice. By being in "fluid communication" is meant that fluid passing through the sample collection area and through the sample collection pad is passed into the absorbent transfer material. The sample collection pad and absorbent transfer material may make direct physical contact, or be slightly apart from one another, but are retained in fluid communication.

The absorbent transfer material can be constructed of a variety of useful absorbent materials. The material should allow the transport of liquid from the collection slide to the test element of the assay device without changing the sample in a manner that interferes with the assay result. Examples of materials suitable for the absorbent transfer material include, but are not limited to, filter paper or other paper-based filter materials, nylon mesh filters, cellulose filters (or filters made of a cellulose-based material), polyester filters, and glass wool filters. In other embodiments the absorbent transfer bead is made of ultra-high molecular weight polyethylene (UHMWPE), polyethylene, polyurethane, nylon, polyester, polypropylene, or polytetrafluoroethylene. In a further embodiment, the transfer material is a filter made of ultra-high molecular weight polyethylene filter.

In various embodiments the absorbent transfer material is treated with reagents that improve the transfer of analyte from the collection slide to a test element of the device. The transfer material can be treated with any of the reagents described herein with respect to treatment of the cover pad and sample collection pad of the collection slide. Examples of reagents that can be used to treat the cover pad, sample collection pad, and absorbent transfer material include, but are not limited to, polyoxyethylene (23) dodecyl ether, polyoxyethylene (9) lauryl alcohol, poly(oxyethylene-cooxypropylene) block copolymer, p-isononylphenoxy-poly(glycidol), sorbitol anhydride monostearate, polydimethylsiloxane methylethoxylate, polyethoxylated (20) oleyl alcohol, polyethoxylated (35) castor oil, polyoxyethelene (20) sorbitan monolaurate, polyoxyethelene (20) sorbitan monolaurate, octylphenol ethoxylate (1.2), octylphenoxypolyethoxy (5) ethanol, octylphenoxypolyethoxy (9-10) ethanol, octylphenoxypolyethoxy (30) ethanol, sodium olefin ($C_{14}$-$C_{16}$) solfonate, sodium polyoxethylene(1)lauryl sulfate, benzalkonium chloride, ethylenediamine alkoxlate block copolymer, 2,4,7,9-tetramethyl-5-decyne-4,7-diol ethoxylate (10), 2,4,7,9-tetramethyl-5-good wetter decyne-4,7-diol ethoxylate (30), amine alkylbenzene sulfonate, poly(oxyethylene-co-oxypropylene) block copolymer, telomer B monoether, sodium dioctylsulfo-succinate, poly(vinylmethylether/maleic anhydride) copolymer, sodium N-oleyl-N-methyltaurate, dodecylsulfate, sodium taurocholate, sodium cholate, N-cytltrimethylammonium bromide, N,N-dimethyldodecylamine N-oxide, 3-[3-(cholamidopropyl)dimethylammonio]-1-proanesulfonate, alcohol ethoxylate, n-octyl sucrose, n-dodecyl sucrose, n-dodecyl maltoside, octyl glucoside, octyl thioglucoside, n-hexyl glucoside, n-dodecyl glucoside, tris (hydroxymethyl) aminomethane buffer, phosphate buffer, borate buffer, tartrate buffer, phthalate buffer, polyvinylpyrrolidone homopolymer, poly(vinylmethylether/maleic anhydride), polyethylene oxide, polyethylene glycol, polyvinylalcohol, 1-ethenyl-2-pyrrolidinone, bony fish gelatin, crosslinked polyacrylic acid polymer, hydroxypropylcellulose, sodium carboxymethylcelluose, sodium polystyrenesulfonate, sodium carageenin, acrylic latex, hydroxyethylcellulose, bovine serum albumin, egg white albumin, casein, 5-chloro-2-methyl-isothiazol-3-one and sodium azide.

As illustrated in FIGS. 2 and 6, a test element 222 is provided with the housing, and in this embodiment is contained within the housing. The test element can be permanently situated within the housing of the device, meaning that it is not removable or insertable in conducting the assay, but is an integral part of the assay device. Referring to FIG. 6, the absorbent transfer bead is in fluid communication with the test element. In one embodiment, the test element is a bibulous test strip suitable for performing a lateral flow assay. A variety of test strips are suitable for use in the assay device. In one embodiment the test strips consist of a bibulous matrix, for example nitrocellulose, and/or other suitable materials. The matrix can have a sample loading zone, a reagent or label zone, and a detection zone. These types of test strips are known in the art and, with reference to the present disclosure, the person of ordinary skill will realize the variety of test strips that are useful in the present invention. In some embodiments a sample loading zone is present at one end of the test strip for the application of sample to the test strip. The sample loading zone is the portion of the test strip in liquid communication with the transfer material. Reagents for conducting the assay or conditioning the sample can also be present at the sample loading zone, or they can be present in a separate reagent or label zone. These reagents can serve a variety of purposes, for example preparing the sample for optimal binding with a specific binding molecule, or improving the stability of an analyte of interest. By "conditioning" a sample is meant adjusting the characteristics of the sample to promote or improve the reaction that detects the presence of the analyte. For example, buffers may be included to adjust the pH of the sample. If the sample contains substances that compete for binding with a specific binding molecule used in the assay, a secondary blocking antibody can be included to bind the substance, or if enzymes that would degrade the specific binding molecules for the analyte are present in the sample, one or more enzyme inhibitors can be added to the reagent zone.

The sample loading zone is present at the upstream end 232 of the test strip. Towards the downstream end of the test strip 234 is the reagent zone, which is followed by a detection zone. The reagent zone can include reagents for conditioning the sample, reagents for labeling the analyte (e.g., specific binding molecules if the assay is a sandwich format immunoassay) or labeled analyte analogs (e.g., if the assay is a competitive format immunoassay). In some embodiments the reagent zone contains a labeled specific binding molecule for the analyte present on the matrix in a dried form, and which can be solubilized by sample fluid as it passes along the matrix. In one embodiment the specific binding molecule is an antibody or fragment thereof. In one embodiment the analyte is human hemoglobin (hHb), and the labeled specific binding molecule is an antibody that binds hHb. The antibody can be labeled by any suitable methods, for example, a metal sol, colored latex beads, and dyes. In some embodiments the sample loading zone and the reagent zone over-lap. In other embodiments there are present a series of reagent zones located on the test strip.

The detection zone is the area of the test strip where the presence of the analyte is detected. In some embodiments the detection zone contains a test line for visually detecting the presence or absence of the analyte of interest at the test line.

The test line can be of any shape, and need not be only a line. The test line can have a specific binding molecule for the analyte. When human hemoglobin is the analyte of interest, the specific binding molecule on the test line binds to hHb. In this embodiment the specific binding molecule binds to human Hb, and does not bind to hemoglobin that might be present from the diet, in order to avoid false positive results.

Methods of Detection

Another aspect of the present invention provides methods of detecting the presence or absence of an analyte in a sample contained in a sample collection slide. In one embodiment of the present method, a collection slide containing the sample is placed into the docking area of an assay device, as shown in FIG. 4. Extraction buffer 512 is applied to the buffer or solvent orifice of the collection slide. The extraction buffer elutes the analyte of interest from the sample, if the analyte is present. Buffer applied to the buffer orifice flows through the cover pad and into the sample collection area containing the dried sample. The dried sample is rehydrated and a portion of the sample elutes out of the collection slide, through the eluent orifice. In one embodiment the buffer is pulled through the collection pad and into the absorbent transfer material by capillary action. Excess buffer eluted from the collection slide is collected in the well surrounding the absorbent transfer material. Eluate within the transfer material flows by capillary action into the application zone of the test strip, and then to the downstream end of the test strip. As the eluate flows from the transfer material into the test strip, excess eluate held in the well may be absorbed and transferred to the test strip, by the transfer material.

As the eluate flows through the sample loading zone and reagent zone of the test strip, it dissolves reagents for conducting the assay present in the loading zone or reagent zone. In one embodiment these reagents are dried on the test strip. Reagents can also be included that condition the eluate for optimal detection, as described above. For example, if the assay is a sandwich format immunoassay reagents may include specific labeled binding molecules for the analyte, such as an antibody or fragment thereof. In one embodiment the specific binding molecule is a gold-labeled anti-hHb antibody or antibody fragment. If the analyte is present in the sample, the labeled specific binding molecule would capture the analyte and form a labeled, soluble complex, which is detected in the detection zone. The eluate continues to flow through the test strip to the detection zone, which contains a test line having specific binding molecules for the analyte. For example, the specific binding molecule can be an unlabeled antibody against the analyte, which binds at an epitope different from that of the labeling reagent. If the assay is a sandwich assay, the specific binding molecule in the test line captures the labeled antibody-analyte complex, and forms a visually detectable line indicating that the analyte is present in the sample. The test result therefore appears in the results window 128 located in the top portion of the housing.

In another embodiment the assay is a competitive format immunoassay. In this embodiment, the label zone or reagent zone of the test strip contains a labeled analog of the analyte, such as a gold-labeled hHb analog. If no analyte is present in the sample, the labeled analyte analog binds the antibody on the test line. Therefore a positive result on the test line indicates that no analyte is present in the sample. When analyte is present, it competes with the labeled analog to bind the antibody on the test line. As the concentration of analyte in the sample increases, the amount of analog that binds to the test line decreases. Therefore, a lighter line or no line indicates the presence of analyte in the sample.

A procedural control can also be included in the detection zone. The procedural control can be present as a line, and will always appear whether or not analyte is present in the sample. Absence of a positive result from the procedural control indicates an invalid assay.

In other embodiments the eluate is tested by means other than an immunoassay. For example, the analyte-containing eluate could be detecting using a chemical means, such as a Guaiac test or other chemical means.

Types of Samples and Analytes

A "sample" is any material to be tested for the presence, absence, or quantity of an analyte. In one embodiment the sample is a biological sample, such as a stool sample. But any type of sample can be assayed using the present invention, as long as it contains an analyte to be detected that can be solubilized and can be passed through the collection slide and into the assay device. The sample can be in many forms, such as solid, semi-solid or highly viscous materials, such as stool, soils, tissues, blood, bodily fluids, or macerated organs. The sample may also be an oral or vaginal swab.

A variety of analytes may be tested for using the present device. Examples of analytes that can be detected using the present invention include, but are not limited to, hemoglobin or other blood components, creatinine, bilirubin, nitrite, protein (nonspecific), hormones (e.g. human chorionic gonadotropin, luteinizing hormone, follicle stimulating hormone, etc.), leukocytes, sugars, heavy metals or toxins, bacterial components (e.g. proteins, sugars, or antigens specific to a particular type of bacteria, such as *E. coli* 0157:H7, *Staph. aureus*, *Salmonella* sp., *Salmonella typhii*, *Shigella*, *C. perfringens*, *Clostridium difficile*, *Campylobacter*, *Helicobacter pylori*, *L. monocytogenes*, *V. parahaemolyticus*, *Vibrio cholerae*, or *B. cereus*), ova and parasites, and physical characteristics of the urine sample, such as pH and specific gravity. Any analyte can be detected for which a reliable assay can be designed. With reference to the present disclosure the person of ordinary skill in the art will realize a variety of antigens that can be detected using a variety of assay principles applicable in the invention.

Test Kits

A further aspect of the present invention provides kits containing one or more collection slides of the present invention, and/or one or more assay devices of the present invention, and instructions for their use in carrying out an assay. The test kits can be packaged in a variety of formats, depending upon the needs of the user. In one embodiment the instructions provided with the kit are instructions for detecting the presence of hemoglobin in a stool sample.

In one embodiment, the kit contains three collection slides, three assay devices, three applicators, a desiccation mailing pouch having three sealable compartments, and instructions for collecting a sample, provided in a package. The package can be any suitable container. In various embodiments the package can be a box, a pouch, a bag, or can be simply a wrapping binding the items of the kit together.

In another embodiment the kits contain one or more collection slides and assay devices individually packaged in foil pouches, and one or more bottles of extraction buffer, and instructions, provided in a package. In another embodiment the kits contain three individually wrapped collection slides, extraction buffer for performing three tests, and instructions for use. At a health care facility where many tests would be conducted, the kit can contain many individually wrapped test devices, one or two large bottles of extraction buffer, and a single copy of the instructions.

A further embodiment provides a kit containing two "mini-kits," wherein one mini-kit contains packaged together three collection slides, three applicators, a desiccant mail pouch and instructions for the patient explaining how to correctly collect the samples. The second mini-kit would contain, packaged together for the doctor, three test devices, extraction buffer sufficient to perform three tests and instructions for use.

Example 1

Effect of Treatment of Transfer Bead with Surfactant on Buffer Flow Rate

This example illustrates the benefit of treating the absorbent transfer material with surfactant (Triton® X-100 (synonyms: octyl phenol ethoxylate, polyoxyethylene, Octyl phenyl ether) in manufacturing the assay device.

Absorbent transfer material in the form of beads was treated with solutions of Tris-casein-PVP buffer containing 0, 1, 2, 3, 4 or 5% Triton® X-100. The saturated transfer beads were then thoroughly dried at 55° C., followed by insertion of each bead into the bead orifice of an assembled test device containing a test strip. Unfilled collection slides having sample pads treated with 0.06 ug Triton® X-100 were engaged with the test devices and 200-240 µl of buffer was applied to each buffer orifice. The time for the control line to appear in the results window was measured. In all cases, the buffer passed through the empty collection slide in 5 seconds. When the transfer bead contained no (0%) Triton® X-100, it took 68 seconds for the control line to appear on the test strips. However, a concentration of 1-5% of Triton® X-100 reduced the time to 19-26 seconds. Therefore, a concentration of 1-5% Triton® X-100 reduces the length of sample flow time substantially.

Example 2

Effect of Collection Slide Cover Pad Surfactant Concentration on Buffer Flow Rate This example illustrates the benefit of treating the collection slide cover pad with surfactant to obtain a faster flow rate of the buffer.

All test devices contained transfer beads treated with 1.2 µg of Triton® X-100. The sample collection pads of the collection slides were untreated. The cover pads were treated with 20 µl of 0, 0.31, 0.63, 1.25, 2.5 or 5% Triton® X-100. The empty collection slides were engaged in the test devices and 200 µl of buffer was added to each buffer orifice, to trigger the lateral flow. Buffer was unable to flow into the collection slide when the cover pad was not treated with a surfactant (0% Triton® X-100). As Triton® X-100 concentration increased, the flow rate also increased. When the cover pad was treated with 0.31% Triton® X-100, the control line appeared at 20 seconds. At Triton® X-100 concentrations of 0.63%, 1.25%, 2.5% and 5%, the control line appeared at 17, 16, 15 and 12 seconds, respectively. However, it was found that at the higher surfactant concentrations (i.e. 1.25% and 5% Triton® X-100) the buffer leaked out of the sample area of the collection slide.

Experiment 3

Influence of Sample Cover Pad and Transfer Bead on Test Sensitivity

This example illustrates the ability of the cover pad and sample collection pad to allow the passage of hemoglobin, and therefore not interfere with assay sensitivity.

Solutions containing 0, 50, 100 and 200 ng hHb/ml were prepared. Collection slides having cover pads treated with 20 µl of 0.53% Triton® X-100 were engaged in the docking area of assay devices of the invention having transfer beads treated with 1.2 µg Triton® X-100. 200 µl of the hHb solutions was applied to the buffer orifices of the collection slides, followed by measurement of the test line intensity at 5 minutes of incubation time. As a control, 140 µl of the hHb solution was applied directly to test strips housed in test devices having no transfer beads. The intensity of the test lines of the control tests was also measured at 5 minutes.

The test samples and the control samples were found to produce the same results. At a concentration of 0 ng hHb/ml, both the test and control produced negative results. At 50 ng hHB/ml both the devices containing the treated pad/bead and the control device produced a low positive signal. At 100 ng hHb/ml both the devices containing the treated pad/bead and the control device produced a medium positive signal. And at 200 ng hHb/ml both the devices containing the treated pad/bead and the control device produced a medium positive signal. Thus, the cover pad and transfer bead do not retain hHb and have no significant effect on the sensitivity of the test.

Example 4

Use of the Collection Slide and Assay Device for Analysis of hBh in Stool

Three collection slides of the invention are prepared by a patient. At a health care facility, each card is placed into the docking area of an assay device of the invention. By placing the collection slides into the docking area, the hinged side of the slide is inserted under the tang, and the slide pressed downward and snapped into place in the docking area, so that the eluent orifice of the collection slide is in fluid communication with the absorbent transfer material of the device.

Three drops (about 200 µl) of extraction buffer are applied to the solvent orifice of the collection slide. During a brief (e.g., 5 minutes) incubation period, the buffer is drawn through the sample collection pad and through the absorbent transfer material, and into the test element of the device, where the detection of the analyte (hHb) occurs. The test element is a test strip having at test line with specific binding molecules for hHb, and a reagent zone with labeled antibodies for hHb. After the incubation period has passed, the detection zone of the assay device is observed and found to exhibit both a control line, and a positive result (red line) at the test line, indicating a positive result for hHb in the stool sample.

The invention illustratively described herein may be practiced in the absence of any element or elements, limitation or limitations that are not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by various embodiments and optional features, modification and variation of the concepts herein disclosed may be resorted to by those skilled in the art, and that such modifications and variations are considered to be within the scope of this invention as defined by the appended claims.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other documents.

The invention claimed is:

1. A method of detecting the presence or absence of an analyte in a sample contained in a sample collection slide, comprising:

placing a collection slide containing the sample into a docking area of a device and transferring the sample from the slide to the device to detect the analyte in the sample, wherein the device comprises:

a docking area for receiving a portion of the collection slide and further comprises a sample transfer orifice with an absorbent transfer material disposed therein in fluid communication with a test element that further comprising a reagent; and a results window for observing a test result of the test sample reacting with the test element; and wherein the collection slide comprises a first water resistant card having a single eluent orifice and no reagent;

a second water resistant card hingeably connected to the first card and having a single solvent orifice and no reagent, the sample is applied to the collection slide when the slide is in an open position, the card is closed after the sample is applied and retains the sample therebetween the solvent and eluent orifices, wherein the single eluent orifice aligns with the single solvent orifice when the first water resistant card is juxtaposed with the second water resistant card;

applying an extraction buffer to the solvent orifice of the collection slide where the extraction buffer to pass through the sample area and into the absorbent transfer material and test element; and observing a test result in the results window.

2. The method of claim 1 wherein the test element comprises, a bibulous matrix comprising a sample application zone in fluid communication with the transfer bead; a reagent zone comprising reagents for conducting an assay; and a detection zone comprising a test line for detecting the presence or absence of the analyte.

3. The method of claim 2 wherein the test line comprises specific binding molecules for the analyte.

4. The method of claim 2 wherein the test line contains reagents for conducting a chemical test.

5. The method of claim 1 wherein the analyte is human hemoglobin.

6. A kit for collecting a biological sample, comprising:

a collection slide comprising: a first water resistant card without a reagent having an inner surface and only a single eluent orifice;

a second water resistant card without a reagent hingeably connected to the first card and having an inner surface and only a single solvent orifice, the collection slide having an open position and a closed position, wherein the single solvent and single eluent orifices are aligned when the collection slide is in the closed position; and a sample collection area on the first water resistant card to which sample is applied for collection, present between the solvent and eluent orifices when the collection slide is in the closed position; and a device for detecting an analyte in a fluid comprising: a housing containing a test element that comprises a reagent, a docking area for engaging a portion of the collection slide and comprising a sample transfer orifice, with an absorbent transfer bead disposed therein and in fluid communication with the test element;

a results window for observing a test result;

a sample collector;

an envelope for containing a loaded collection device; and instructions for use; provided in a package.

7. A kit according to claim 6 further comprising one or more bottles containing buffers for conducing an assay according to the instructions for use.

* * * * *